(12) United States Patent
Blum

(10) Patent No.: US 6,737,257 B2
(45) Date of Patent: May 18, 2004

(54) HYPERTHERMOPHILIC ENZYMES FOR INDUSTRIAL CHEMICAL REDOX REACTIONS: A METHOD FOR BIOFUEL ETHANOL PRODUCTION

(75) Inventor: Paul Blum, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/968,151

(22) Filed: Oct. 1, 2001

(65) Prior Publication Data

US 2002/0037564 A1 Mar. 28, 2002

Related U.S. Application Data

(63) Continuation-in-part of application No. 09/313,275, filed on May 18, 1999, now abandoned.
(60) Provisional application No. 60/085,873, filed on May 18, 1998.

(51) Int. Cl.$^7$ .................................................. C12P 7/02
(52) U.S. Cl. ........................ 435/155; 435/41; 435/90; 435/156; 435/157; 435/161
(58) Field of Search ........................ 435/155, 41, 90, 435/156, 157, 161

(56) References Cited

PUBLICATIONS

Wong et al (J. Am. Chem. Soc. 107:4028–4031 (1985)).*
Rella et al (Eur. J. Biochem. 167:475–479 (1987)).*
Giardina et al (Biochem. J. 239:517–522 (1996)).*
De Rosa et al (Biochem. J. 224:4017–414 (1984)).*

Definitions of "hyperthermophile" and "hyperthermophili", Biotech Life Science Dictionary, BioTech Resources, Indiana University, 1998; available on website: http://biotech.icmb.utexas.edu/search/dict–search.phtml (1 page).

Definition of "mesophile", Biotech Life Science Dictionary, BioTech Resources, Indiana University, 1998; available on website: http://biotech.icmb.utexas.edu/search/dict–search.phtml (1 page).

Balows, Albert, et al. eds., The Prokaryotes, 2d Edition, Springer–Verlag, New York, 1992, p. 84.

Tortora Gerard, J., Microbiology: An Introduction, 5th Edition, Benjamin/Cummings Publishing Company, Inc., 1995, p. 144.

Madigan, Michael T., et al., Brock Biology of Microorganisms, 9th Edition, Prentice Hall, Upper Saddle River, New Jersey, pp. 147–148.

Woodward, Jonathan, et al., "In vitro hydrogen production by glucose dehydrogenase and hydrogenase," Nature Biotechnology, Jul., 1996, 14:872–874.

* cited by examiner

Primary Examiner—Francisco Prats
(74) Attorney, Agent, or Firm—Jondle & Associates PC

(57) ABSTRACT

The present invention is directed to use of hyperthermophilic enzymes for industrial chemical redox reactions such as ethanol production. The present invention is especially useful for the coupled synthesis and recovery of alcohols whereby recovery of alcohol is simplified.

17 Claims, 10 Drawing Sheets

HYPERTHERMOPHILIC ENZYMES FOR INDUSTRIAL CHEMICAL REDOX REACTIONS: A METHOD FOR BIOFUEL ETHANOL PRODUCTION

This application is a continuation-in-part of U.S. patent application Ser. No. 09/313,275 filed May 18, 1999, now abandoned, which is related to U.S. provisional patent application Ser. No. 60/085,873 filed May 18, 1998, incorporated herein by reference.

BACKGROUND OF INVENTION

The present invention is directed to a method for use of enzymes from hyperthermophilic Archaea in the production of product at the expense of added carbon while recycling pyridine nucleotides. In a preferred method of the invention, the enzymes used are glucose dehydrogenase and alcohol dehydrogenase and the product is an alcohol or aldehyde. In the most preferred embodiment both enzymes are from *Sulfolobus solfataricus*; glucose dehydrogenase is derived directly from *S. solfataricus*, and the alcohol dehydrogenase is in a recombinant form. Using the method of invention, generation of alcohol from carbohydrate can be accomplished at elevated temperatures which simplify the recovery (facilitate the removal) of alcohol by volatilization, thereby driving the reaction toward production of additional alcohol.

The publications and other materials used herein to illuminate the background of the invention, and in particular cases, to provide additional details respecting the practice, are incorporated by reference, and for convenience are referenced in the following text by author and date and are listed alphabetically by author in the appended bibliography.

The production of many amino acids such as L-alanine, leucine and glutamate have been accomplished using enzymes that regenerate pyridine nucleotides (Hasumi, et al., 1995; Hasumi, et al., 1996; Itozawa, et al., 1995). In some cases, pyridine nucleotides have been regenerated with the bioreduction of carbonyl compounds (Itoh, et al., 1992; Itozawa, et al., 1995). The regeneration methods used include electricity (Fassouane, et al., 1990) and enzymes (Woodward, et al., 1996). Enzymes which have been used in the regeneration of pyridine nucleotides include glucose dehydrogenase from *Thermoplasma acidophilum* (Woodward, et al., 1996) and alcohol dehydrogenase from horse liver (Tsuji, et al., 1994).

Current efforts to improve biofuel ethanol production focus on fermentation technology. Large reactor volumes in the conventional production methods are required however to achieve dilute ethanol concentrations needed to overcome microbial ethanol sensitivity. Fermentative synthesis therefore typically continues until the concentration of product is toxic to the microbial population; synthesis is then complete and a separate process is undertaken to recover product. This creates additional constraints on ethanol recovery.

Enzymatic approaches to ethanol synthesis preferably utilize enzymes that have broad substrate specificity, accept several cofactors and which are active and stable at the room temperatures typically employed. Enzymes can be inactivated in a number of ways, such as denaturation (heat or solvent), oxidation and dissociation. Additional considerations are necessary when the enzyme used for conversion of substrate to desired product is reversible and/or affected by product accumulation. Current efforts to address inactivation by product accumulation include monitoring progress of the reaction by measuring substrate concentration (Wong et al., 1985) and other reaction parameters such as temperature, rate and cofactor concentrations. The duration of the synthesis process is therefore limited because the reaction must be stopped before accumulated product inactivates the enzymes. The choice of recovery method depends upon the product to be recovered, for example, recovery of product may be by chemical extraction (Wong et al., 1985) or it may involve semipermeable membranes.

Because industrial synthesis cannot typically proceed under the conditions necessary for recovery of product, recovery is undertaken after synthesis is complete. Thus, it is desirable to establish new methodologies, which simplify the process of synthesis and increase recovery of product and which are capable of overcoming microbial sensitivity to product formation. The present invention solves this need as illustrated herein.

SUMMARY OF THE INVENTION

The present invention is directed to a method for use of enzymes from hyperthermophilic Archaea in the production of product at the expense of added carbon while recycling pyridine nucleotides. In a preferred method of the invention, the enzymes used are glucose dehydrogenase and alcohol dehydrogenase and the product is an alcohol or aldehyde. In the most preferred embodiment, both enzymes are from *Solfolobus solfataricus*; glucose dehydrogenase is derived directly from *S. solfataricus*, and the alcohol dehydrogenase is in a recombinant form. Using the method of invention, generation of alcohol from carbohydrate can be accomplished at elevated temperatures which simplify the recovery (facilitate the removal) of alcohol by volatilization, thereby driving the reaction toward production of additional alcohol.

DETAILED DESCRIPTION OF THE INVENTION

Figure 1:
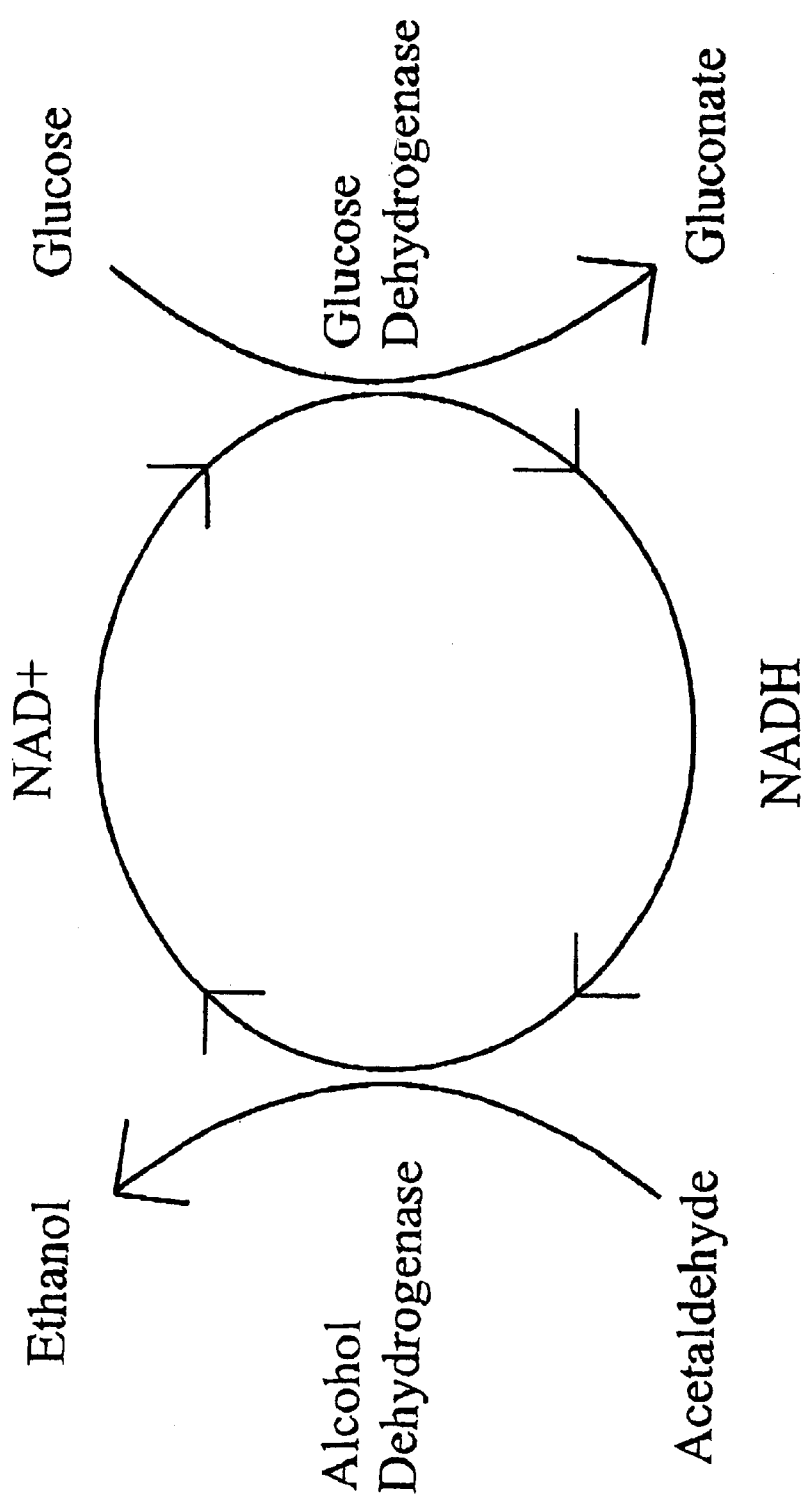
FIG. 1 illustrates use of the method of the invention for conversion of glucose to ethanol.

The present invention is directed to a method for use of enzymes from hyperthermophilic Archaea in the production of product at the expense of added carbon while recycling pyridine nucleotides. In a preferred method of the invention, the enzymes used are glucose dehydrogenase and alcohol dehydrogenase and the product is an alcohol or aldehyde. In the most preferred embodiment, both enzymes are derived from *Sulfolobus solfataricus*; glucose dehydrogenase is derived directly from *S. solfataricus*, and the alcohol dehydrogenase is in a recombinant form. Using the method of invention, generation of alcohol from carbohydrate can be accomplished at elevated temperatures which simplify the recovery (facilitate the removal) of alcohol by volatilization, thereby driving the reaction toward production of additional alcohol.

*Solfolobus solfataricus* is a hyperthermophilic archaeon, which can be found in acidic hot springs around the world (Haseltine, et al., 1996); Rolfsmeier and Blum, 1995; Rolfsmeier, et al., 1998). Survival in this extreme environment is, in part, a consequence of the fact that the enzymes from this archaeon are unusually stable at these elevated temperatures. Hyperthermophilic enzymes from *S. solfataricus* are representative, however, bacterial or other archaeal glucose dehydrogenases may also be used in the practice of the present invention. For example, hyperthermophilic enzymes purified from thermoacidophiles are equal in their thermostability, temperature optimum and pH optimum (Bright et al., 1993; Pulich et al., 1976; Selig et al., 1997). This ability to withstand extreme environments, such as high temperatures, makes hyperthermophilic enzymes desirable for industrial applications. The cell-free high temperature method of the present invention has been developed using hyperthermophilic enzymes. Discovery of the present method makes possible the coupled synthesis and recovery of product and overcomes problems which restrict current alcohol production efforts, such as inactivation by product accumulation and microbial ethanol sensitivity.

Hyperthermophilic alcohol dehydrogenase (ADH) and glucose dehydrogenase (GDH) from the hyperthermophilic archaea, *S. solfataricus*, were used to model critical reaction parameters including temperature, rate, substrate and cofactor concentrations. Rella et al., demonstrated that an activity exists in sulfolobus which can oxidize a range of alcohols, but only a single aldehyde (anisaldehyde) and did not demonstrate the activity to reduce acetaldehyde to for alcohol. Based on Rella et al., these enzymes would work to form aldehydes, at the expense of gluconic acid reduction. It has been discovered that the activity of this enzyme can reduce acetaldehyde to form ethanol in a directed fashion. Carbohydrates which can serve as substrates for the GDH of *S. solfataricus*, include D-idose, D-xylose and D-glucose. For purposes of description, D-glucose was used to model the oxidation of carbohydrates by GDH. These enzyme reactions are able to take place at the boiling point of ethanol. As a result, ethanol synthesis is coupled to recovery (distillation). Recovery therefore results from volatilization of ethanol.

If the enzyme used for conversion of substrate to desired product is reversible and/or affected by product accumulation, as determined herein for ADH from *S. solfataricus* (example 3), synthesis must be separated (in time) from recovery of product. As a consequence, the synthesis reaction is conventionally taken to completion and recovery is later undertaken. The discovery of the present method for coupling synthesis and recovery of product, as taught in the instant application, addresses problems associated with conventional methods. With the instant invention, synthesis and recovery can occur at the same time, thereby simplifying the recovery of product. A further advantage of the present method is that the removal of product drives the reaction toward production of additional product.

Definitions

The present invention employs the following definitions:

"Archaea" refers to a group of prokaryotes distinct from bacteria and encompassing hyperthermophilic, halophilic and methanogenic organisms.

"Cell-free Synthesis" refers to the use of cell extracts containing enzymes used to catalyze particular chemical reactions.

"Coupled Oxidation-Reduction" refers to enzyme-mediated change in the redox status of one chemical substrate which is accompanied by another enzyme-mediated change in the redox status in the opposite direction of a second chemical substrate.

"Coupled synthesis and recovery" and "synthesis coupled to recovery" of product (and the like) refer to the method of the present invention, whereby the enzyme reactions are able to take place at or above the boiling point of the product, and as a consequence, recovery of product by volatilization is able to take place at the same time as synthesis. Synthesis and recovery are thereby coupled and product can be continuously recovered.

"Elevated Temperature" refers to the range of temperatures within which the enzyme retains significant activity under the atmospheric conditions under the existing atmospheric condition.

"Hyperthermophilic" refers to a general term for microorganisms which have a temperature range of growth which falls within the range of about 65 degrees Centigrade to about 115 degrees Centigrade. Hyperthermophilic is sometimes also used herein to refer to enzymes produced by hyperthermophilic microorganisms. For example *S. solfataricus* has a temperature range of growth of about 65° C. to about 91° C.

"Pyridine Nucleotide Regeneration" refers to enzyme-mediated renewal of the reduced form of an enzyme cofactor (pyridine nucleotide) by coupled oxidation of a second chemical.

EXAMPLES

The following examples are illustrative of the present invention and are not intended to limit the scope of the invention. Standard techniques well-known in the art or the techniques specifically described below are utilized.

Example 1

Enzyme Preparation and Assay

The gene for *S. solfataricus* alcohol dehydrogenase was cloned, sequenced and expressed in *Escherichia coli* from which the enzyme was purified and assayed as described in Rella, et al. (1987). Glucose dehydrogenase from *S. solfataricus* was purified and assayed as described in Giardina, et al. (1986).

Example 2

Oxidation of Carbohydrates Catalyzed by Glucose Dehydrogenase from *S. solfataricus*

Figure 2:
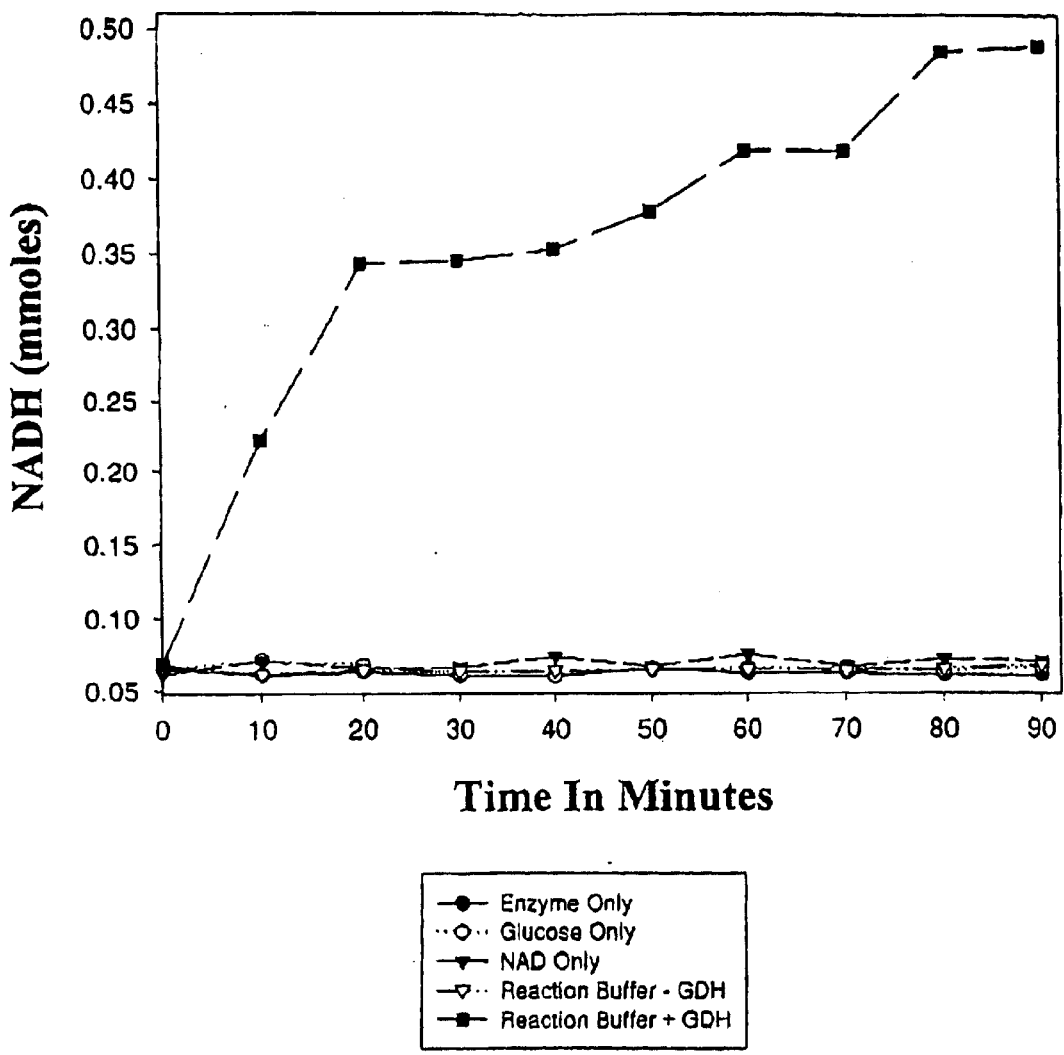
FIG. 2 shows the dependency of GDH activity on substrate and enzyme.
Figure 3:
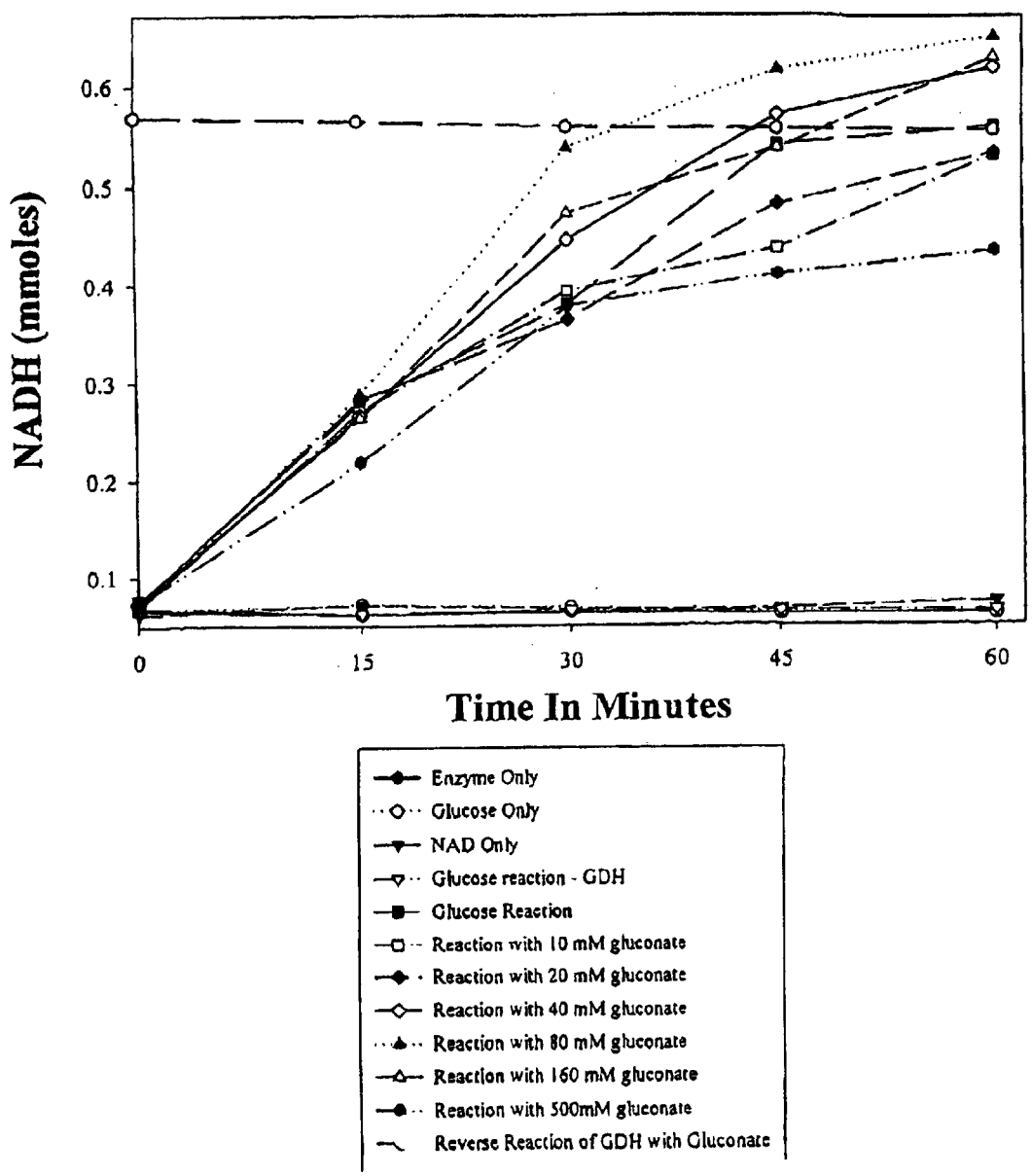
FIG. 3 shows that GDH activity is not reversible and that it is insensitive to feedback inhibition.

*S. solfataricus* metabolizes glucose and other monosaccharides to the corresponding glyconic acid through the action of glucose dehydrogenase (GDH). This pyridine-dependent enzyme uses either $NAD^+$ or $NADP^+$ as a coenzyme, with a preference for $NADP^+$. Carbohydrates which can serve as substrates for GDH from *S. solfataricus* using NAD⁺-dependent oxidation include D-idose, D-xylose, and D-glucose with D-glucose being oxidized at the highest rate (Giardina, et al., 1986). Glucose was degraded by GDH from *S. solfataricus* and the coenzyme NAD⁺, resulting in oxidation of glucose to gluconate. The conversion of glucose to gluconate is substrate and enzyme dependent (FIG. 2). The GDH activity is not reversible and is insensitive to feedback inhibition (FIG. 3).

Example 3

Reduction of Aldehydes Catalyzed by Alcohol Dehydrogenase from *S. solfataricus*

Figure 4:
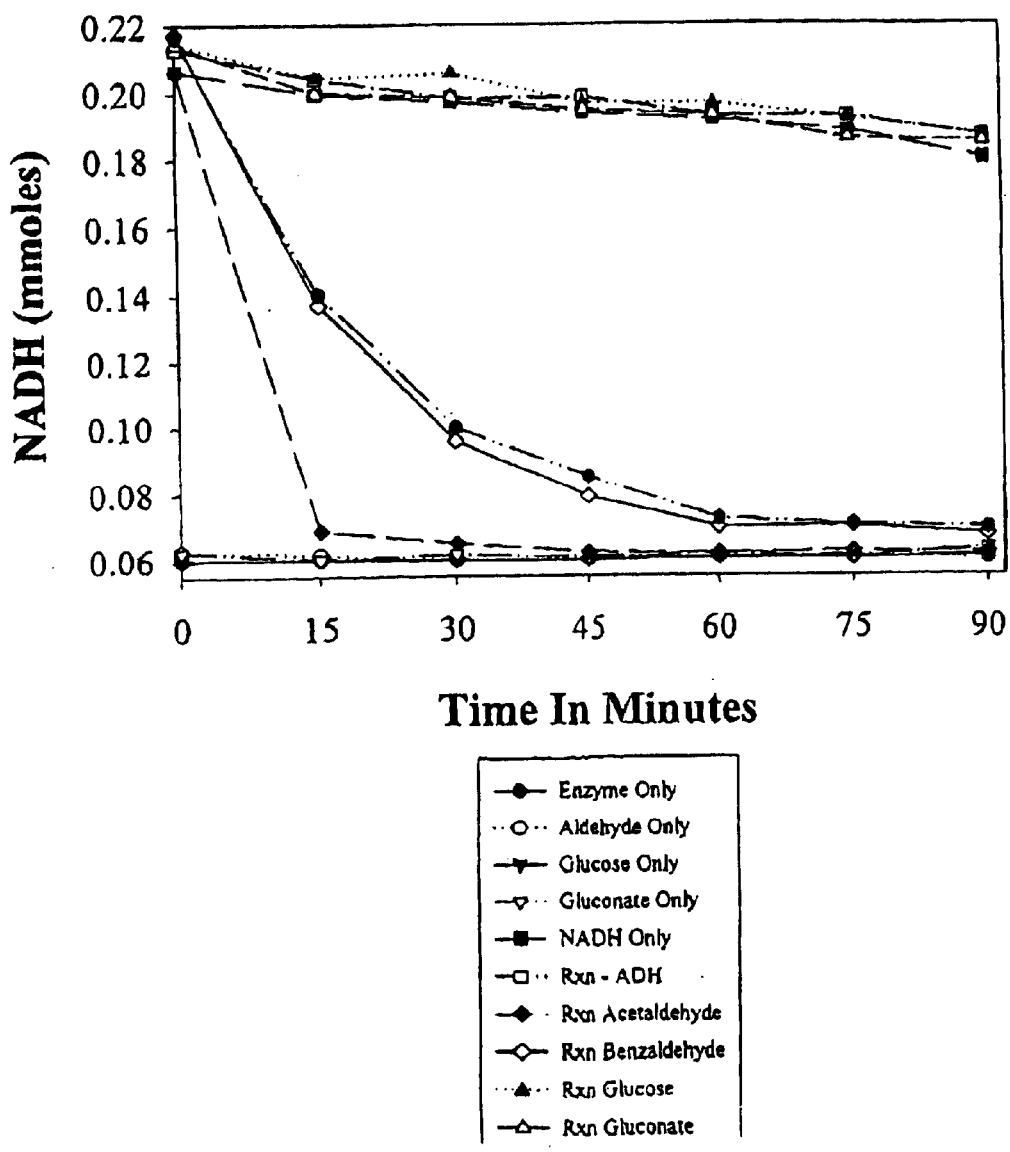
FIG. 4 shows that ADH activity is substrate and enzyme dependent. It also shows the activity of ADH with various aldehydes.
Figure 5:
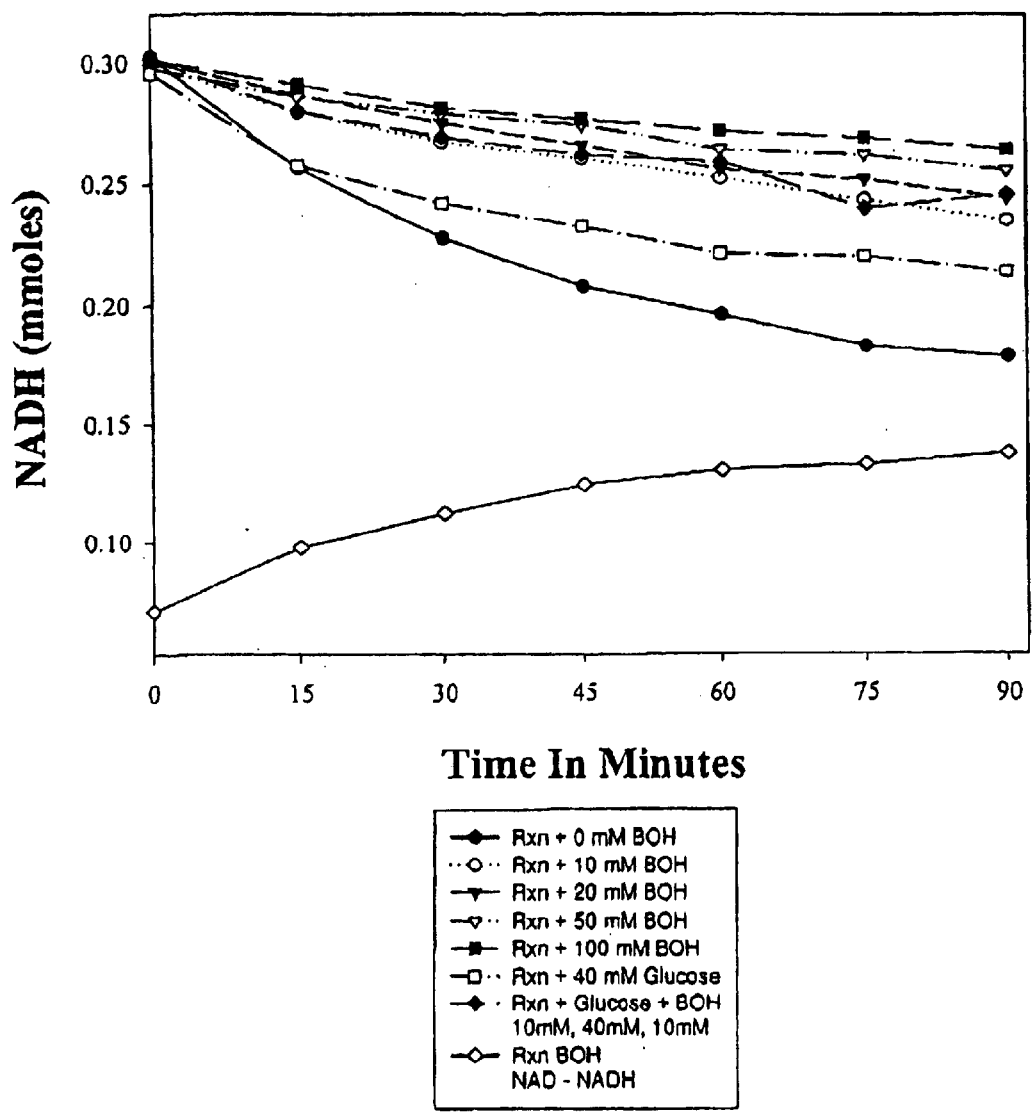
FIG. 5 shows the effects of alcohol accumulation on ADH activity.

Alcohol dehydrogenase (ADH) catalyzes the reduction of aldehydes to their corresponding alcohols (or aromatic or aliphatic aldehydes). The ADH produced by *S. solfataricus* is able to catalyze the production of aromatic alcohols in addition to aliphatic compounds (FIG. 4). The conversion is substrate and enzyme dependent (FIG. 4). Furthermore, the process of conversion of aldehydes by *S. solfataricus* ADH is reversible and affected by product accumulation. Product removal is necessary for directionality of the action of ADH (FIG. 5).

Example 4

Figure 6:
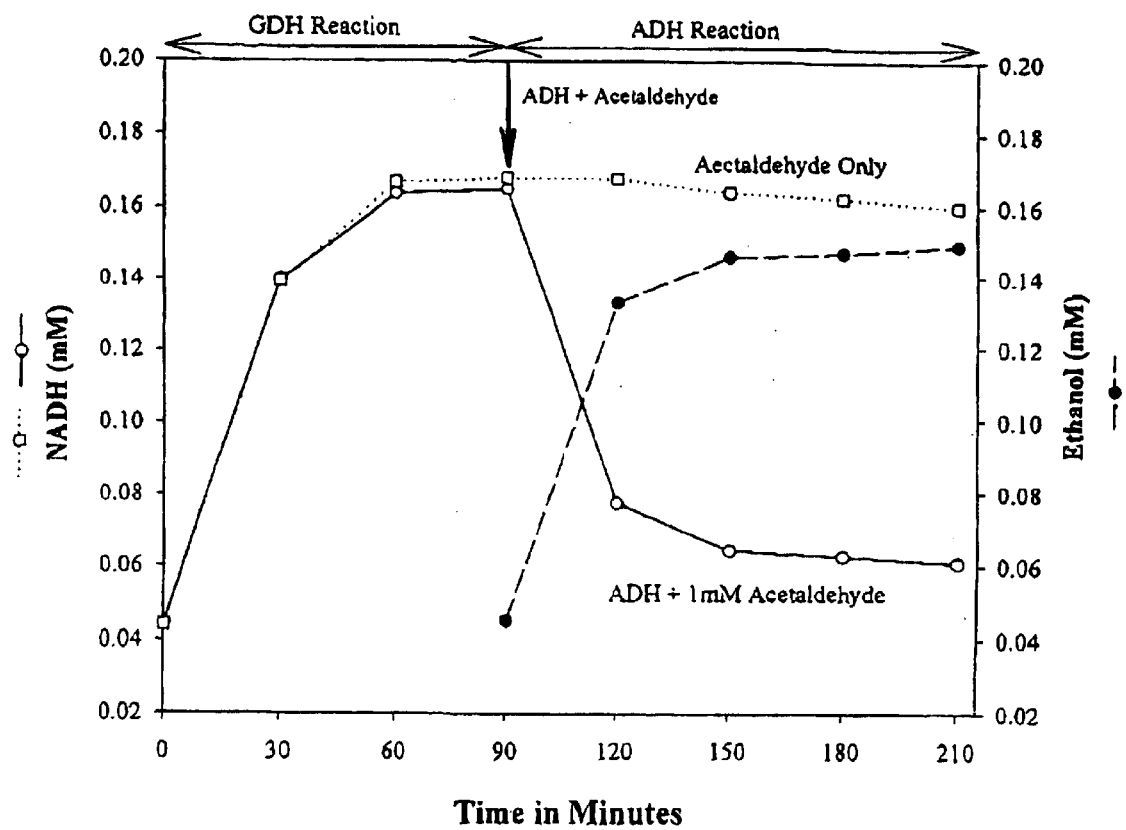
FIG. 6 shows ethanol synthesis by coupled glucose oxidation.
Figure 7:
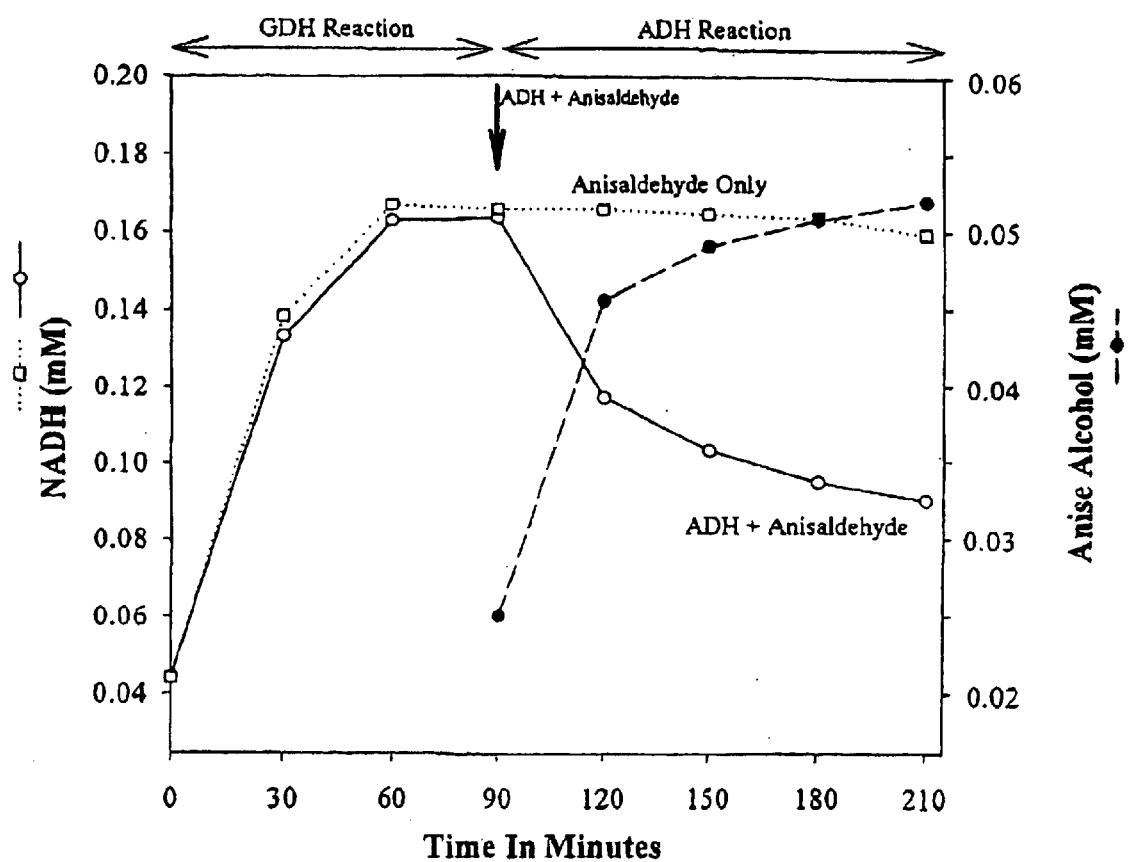
FIG. 7 shows anise alcohol synthesis by coupled glucose oxidation.

Synthesis of Ethanol and Other Alcohols Utilizing A Regenerating Cell-Free-System The combination of GDH and ADH from *S. solfataricus* was used to generate alcohol from glucose. Alcohol synthesis occurred concomitantly with recyclization of NAD⁺/NADH (FIG. 6). Synthesis of other alcohols, including the aromatic, anise alcohol, was also accomplished (FIG. 7). The continuous production of ethanol was achieved with the cell-free, pyridine nucleotide-regenerating method of the invention.

While the synthesis and recovery was undertaken at an essentially constant temperature of about 75° C. to about 80° C., it will be recognized by one skilled in the art that all or some of the reaction components can be combined at temperatures below the boiling point of alcohol and subsequently the temperature raised to volatilize, and therefore recover, the product. Likewise it will be recognized that the temperature of reaction can be undertaken or raised to temperatures above the boiling point of the product. These and other combinations are contemplated within the scope of the present invention.

Example 5

Multiple Cycles of Regenerating NAD⁺/NADH

Figure 8:
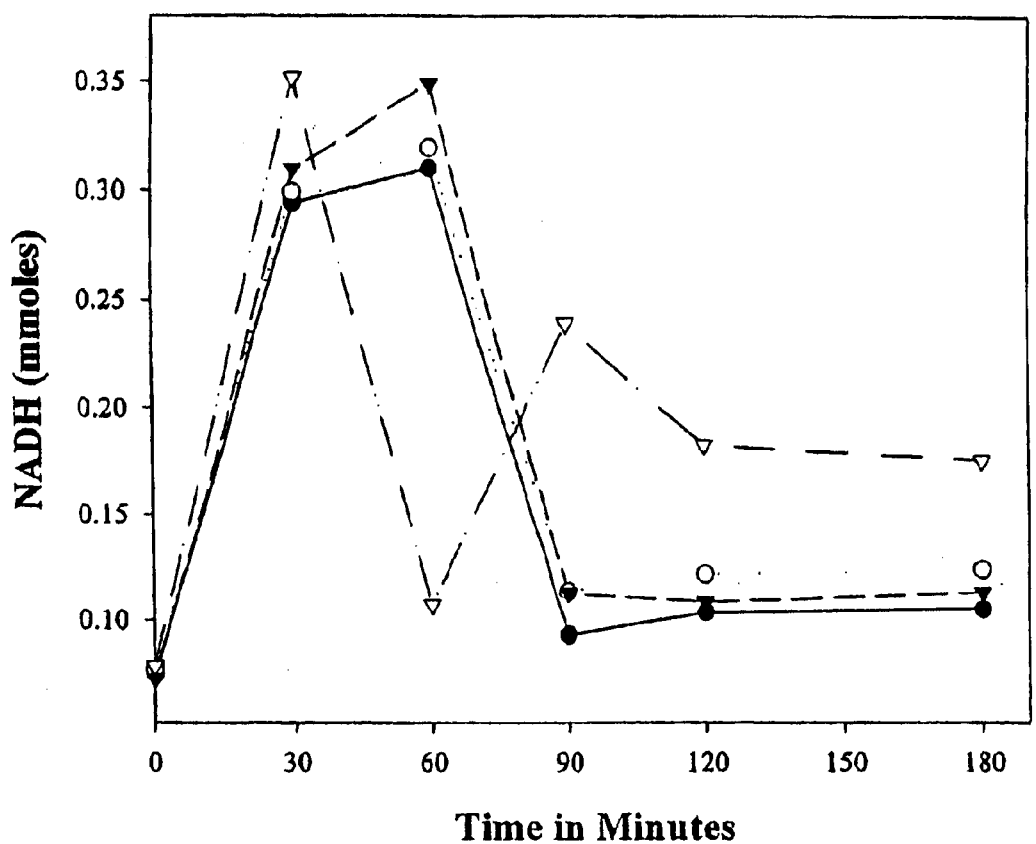
FIG. 8 shows Trial I—multiple cycles of regenerating pyridine nucleotides using acetaldehyde. The data were plotted as the absorbance of NADH at 340 nm over time.
Figure 9:
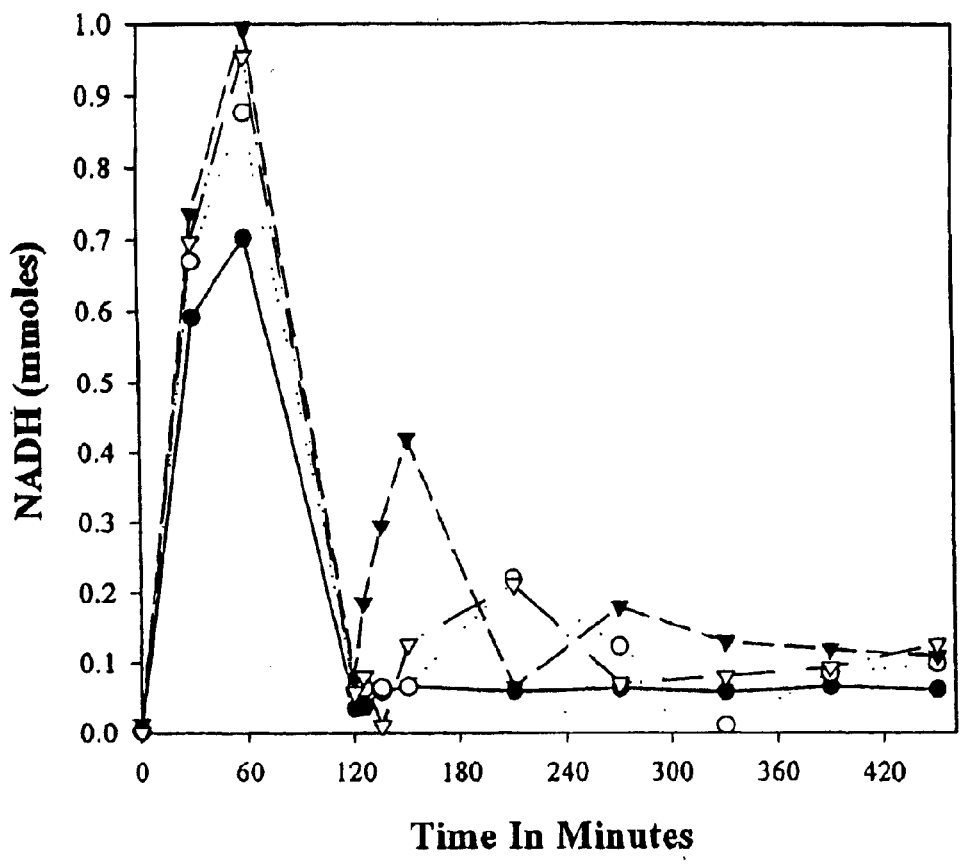
FIG. 9 shows Trial II—multiple cycles of regenerating pyridine nucleotides using acetaldehyde. The data is plotted as the amount of NADH produced over time.
Figure 10:
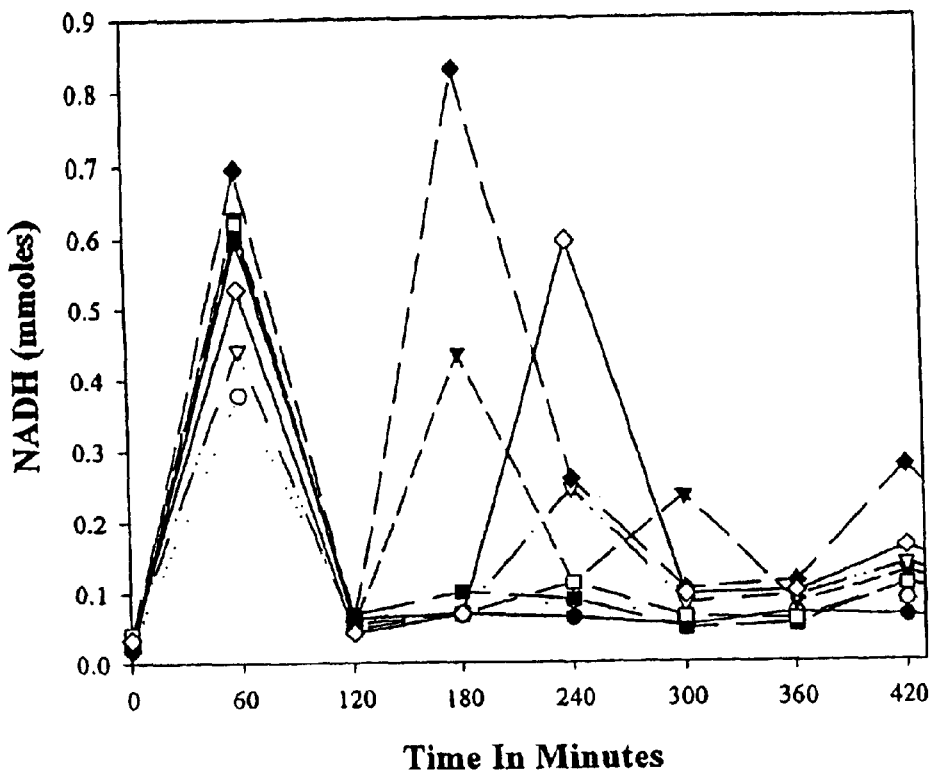
FIG. 10 shows Trial III—multiple cycles of regenerating pyridine nucleotides using acetaldehyde. The graph is plotted as the amount of NADH produced over time.

Multiple regeneration cycles of pyridine nucleotides, NAD⁺/NADH, were accomplished with the readdition of substrates glucose and acetalydehyde and the removal of ethanol (FIGS. 8, 9, and 10).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

BIBLIOGRAPHY

Bright, J. R., et al. (1993). "Cloning, Sequencing, and Expression of the Gene Encoding Glucose Dehydrogenase from the Thermophilic Archaeon *Thermoplasma acidophilum*", 211:549–554.

Fassouane, A., et al. (1990). "Electrochemical Regeneration of NAD in a Plug-Flow Reactor," *Biotechnology and Bioengineering*. 35:935–939.

Fujii, T., et al. (1991). "Modeling of Hollow-Fiber Capillary Reactor for the Production of L-Alanine with Coenzyme Regeneration", *Biotechnology and Bioengineering*. 38:1166–1172.

Giardina, P., et al. (1986). "Glucose Dehydrogenase from the Thermoacidophilic Archaebacterium *Sulfolobus solfataricus*", *Biochemistry Journal* 239:517–522.

Haseltine, C., et al. (1996). "The glucose effect and regulation of alpha-amylase synthesis in the hyperthermophilic archaeon *Sulfolobus solfataricus*", *Journal of Bacteriology*. 178:945–950.

Hasumi, F., et al. (1995). "Synthesis of Glutamate by Reductive Amination of 2-Osoglutarate with the Combination of Hydrogenase and Glutamate Dehydrogenase," *Applied Biochemistry and Biotechnology*. 55:1–4.

Hasumi, F., et al. (1996). "Synthesis of Alanine and Leucine by Reductive Amination of 2-Oxoic Acid with Combination of Hyrogenase and Dehydrogenase", *Applied Biochemistry and Biotechnology*. 56:341–344.

Itoh, S., et al. (1992). "Efficient NAD⁺-Recycling System for ADH-Catalysed Oxidation in Organic Media", *Journal of the Chemical Society, Perkin Transaction I*. 10:3253–3254.

Itozawa, T., et al. (1995). "Immobilization of HLADH on Polymer Materials for Reduction of Cyclohexanone with NADH Regeneration Under Two-Phase Conditions", *Journal of Fermentation and Bioengineering*. 80:30–34.

Livers, K., et al. "A novel method for the production of ethanol using hyperthermophilic enzymes", (Manuscript in preparation).

Pulich, W. M., et al. (1976). "Purification and Characterization of Glucose Dehydrogenase from a Heterotrophically Grown Blue-Green Alga", *Plant Physiology*. 58:393–397.

Rella, R., et al. (1987). *European Journal of Biochemistry*. 167:475–479.

Rolfsmeier, M., and Blum, P. (1995). "Purification and Characterization of a Maltase from the Extremely Thermophilic Crenarchaeote *Sulfolobus solfataricus*", *Journal of Bacteriology*. 177:482–485.

Rolfsmeier, M., et al. (1998). "Molecular Characterization of the α-Glucosidase Gene (malA) from the Hyperthermophilic Archaeon *Sulfolobus solfataricusl*", *Journal of Bacteriology*. 180:1287–1295.

Selig, M. K., et al. (1997). "Comparative Analysis of Embden-Meyeroff and Entner-Doudoroff Glycolytic Pathways in Hyperthermophilic Archaea and the Bacterium Thermotoga", *Archives of Microbiology*. 167:217–232.

Tsuji, Y., et al. (1994). "Enantioselective Dehydrogenation of β-Hydroxysilanes by Horse Liver Alcohol Dehydrogenase with a Novel In-Situ NAD⁺ Regeneration System", *Applied Microbiology and Biotechnology*. 41:219–224.

Woodward, J. S., et al. (1996). "In Vitro Hydrogen Production by Glucose Dehydrogenase and Hydrogenase", *Nature Biotechnology*. 14:872–874.

What is claimed is:

1. A method for coupled synthesis and recovery of alcohol at or above a temperature of about 65° C. comprising: coupled enzymatic oxidation-reduction of substrate, removal of product by volatilization, and regeneration of pyridine nucleotides, wherein the oxidoreductase enzymes are from hyperthermophilic Archaea.

2. The method of claim 1 wherein said alcohol is an aliphatic alcohol.

3. The method of claim 2 wherein said aliphatic alcohol is ethanol.

4. The method of claim 1 wherein said alcohol is an aromatic alcohol.

5. The method of claim 4 wherein the aromatic alcohol is anise alcohol.

6. The method of claim 1 wherein the substrate comprises a monosaccharide.

7. The method of claim 6 wherein the monosaccharide is selected from the group consisting of D-idose, D-xylose, D-glucose and combinations thereof.

8. The method of claim 1 wherein the pyridine nucleotides are selected from the group consisting of NAD and NADP.

9. The method of claim 1 wherein said hyperthermophilic Archaeon is a Sulfolobus species.

10. The method of claim 9 wherein said Sulfolobus species is Sulfolobus solfataricus.

11. The method of claim 1 wherein said oxidoreductase enzymes are glucose dehydrogenase and alcohol dehydrogenase.

12. The method of claim 10 wherein said oxidoreductase enzymes are.

13. The method of claim 12 wherein substrate undergoing oxidation is monsaccharide and the substrate undergoing reduction is aldehyde.

14. The method of claim 13 wherein the monsaccharide is selected from the group consisting of: D-idose, D-xylose, D-glucose, and combinations thereof, and wherein the aldehyde is selected from the group consisting of acetaldehyde, anisaldehyde, benzaldehyde, and combinations thereof.

15. The method of claim 1 wherein said hyperthermophilic Archaeal enzymes are produced naturally or recombinantly.

16. The method of claim 1 further comprising the addition of further substrate, whereby pyridine nucleotides are regenerated and additional product recovered.

17. A method for coupled synthesis and recovery of alcohol at or above a temperature of about 65° C. comprising: coupled enzymatic oxidation-reduction of substrate, removal of product by volatilization, and regeneration of pyridine nucleotides, wherein the oxidoreductase enzymes are from hyperthermophilic bacteria.

* * * * *

UNITED STATES PATENT AND TRADEMARK OFFICE
CERTIFICATE OF CORRECTION

| | | |
|---|---|---|
| PATENT NO. | : 6,737,257 B2 | Page 1 of 1 |
| APPLICATION NO. | : 09/968151 | |
| DATED | : May 18, 2004 | |
| INVENTOR(S) | : Paul Blum | |

It is certified that error appears in the above-identified patent and that said Letters Patent is hereby corrected as shown below:

In column 1 after the paragraph referencing the related applications in the Specification, please insert the following statement which should read
--Statement Regarding Federally Sponsored Research and Funding: This invention was made with U.S. Government support under Grant No. MCB9604000 awarded by the National Science Foundation. The government has certain rights in this invention.--

Signed and Sealed this

Sixth Day of May, 2008

JON W. DUDAS
*Director of the United States Patent and Trademark Office*